United States Patent
Schoenhoeffer et al.

(10) Patent No.: US 9,066,814 B2
(45) Date of Patent: Jun. 30, 2015

(54) IMPLANT ASSEMBLY HAVING AN ANGLED HEAD

(75) Inventors: Helmut Schoenhoeffer, Wildwood, MO (US); Carl Michael Nilsson, Cleveland Heights, OH (US)

(73) Assignee: ULRICH MEDICAL USA, INC., Chesterfield, MO (US)

( * ) Notice: Subject to any disclaimer, the term of this patent is extended or adjusted under 35 U.S.C. 154(b) by 551 days.

(21) Appl. No.: 12/848,593

(22) Filed: Aug. 2, 2010

(65) Prior Publication Data

US 2012/0029635 A1 Feb. 2, 2012

(51) Int. Cl.
*A61F 2/44* (2006.01)
*A61F 2/46* (2006.01)
*A61F 2/30* (2006.01)

(52) U.S. Cl.
CPC .................. *A61F 2/4465* (2013.01); *A61F 2/44* (2013.01); *A61F 2/4611* (2013.01); *A61F 2002/3024* (2013.01); *A61F 2002/30484* (2013.01); *A61F 2002/30525* (2013.01); *A61F 2002/30538* (2013.01); *A61F 2002/3055* (2013.01); *A61F 2002/30579* (2013.01); *A61F 2002/30601* (2013.01); *A61F 2002/30787* (2013.01);
(Continued)

(58) Field of Classification Search
CPC ................................. A61F 2/44–2/46
USPC ............. 623/17.11–17.16; 606/86 A, 90, 99, 606/105; 81/54, 57.42, 177.1, 177.6
See application file for complete search history.

(56) References Cited

U.S. PATENT DOCUMENTS

| 5,571,192 A | 11/1996 | Schönhöffer |
| 5,911,701 A | 6/1999 | Miller et al. |

(Continued)

FOREIGN PATENT DOCUMENTS

| DE | 4012622 C1 | 7/1991 |
| EP | 1 442 729 A1 | 8/2004 |

(Continued)

OTHER PUBLICATIONS

Annex to Form PCT/ISA/206 Communication Relating to the Results of the Partial International Search; PCT/EP2011/062983; Oct. 28, 2011; (2 pages).

(Continued)

*Primary Examiner* — Mary Hoffman
*Assistant Examiner* — Michelle C Eckman
(74) *Attorney, Agent, or Firm* — Jay J. Hoette; The Small Patent Law Group, LLC

(57) ABSTRACT

An implant assembly includes an implant having an upper element and a lower element coaxially aligned with one another. The upper and lower elements are configured to be displaced relative to one another along a longitudinal axis of the implant. The implant assembly also includes a setting tool having a cassette and a tool body. The cassette has a housing, a gear held by the housing, and a drive shaft driving the gear. The cassette holds the implant such that the gear engages the implant to displace the upper and lower elements relative to one another. The tool body has an inner portion and an outer portion being angled relative to one another. The cassette is mounted to the inner portion. The tool body has an outer shaft and an inner shaft rotatable received in the outer shaft. The inner shaft includes a flexible joint at the intersection of the inner and outer portions. The inner shaft drives the drive shaft of the cassette.

31 Claims, 12 Drawing Sheets

(52) U.S. Cl.
CPC ............ *A61F2002/30841* (2013.01); *A61F 2002/4475* (2013.01); *A61F 2002/4624* (2013.01); *A61F 2002/4635* (2013.01); *A61F 2002/4638* (2013.01); *A61F 2220/0025* (2013.01); *A61F 2230/0069* (2013.01); *A61F 2250/0006* (2013.01)

(56) References Cited

U.S. PATENT DOCUMENTS

| | | | |
|---|---|---|---|
| 6,015,436 | A | 1/2000 | Schönhöffer |
| 6,190,413 | B1 | 2/2001 | Sutcliffe |
| 6,190,414 | B1 * | 2/2001 | Young et al. ............... 623/17.15 |
| 6,689,132 | B2 | 2/2004 | Biscup |
| 6,752,832 | B2 | 6/2004 | Neumann |
| 6,764,491 | B2 | 7/2004 | Frey et al. |
| 6,875,237 | B2 | 4/2005 | Dye |
| 7,226,483 | B2 | 6/2007 | Gerber et al. |
| 7,473,267 | B2 | 1/2009 | Nguyen et al. |
| 7,534,266 | B2 | 5/2009 | Kluger |
| 7,575,580 | B2 | 8/2009 | Lim et al. |
| 7,635,368 | B2 | 12/2009 | Errico et al. |
| 7,635,371 | B2 | 12/2009 | McGahan et al. |
| 7,651,515 | B2 | 1/2010 | Mack et al. |
| 2004/0098129 | A1 | 5/2004 | Lin |
| 2004/0153065 | A1 * | 8/2004 | Lim ................................. 606/53 |
| 2004/0172036 | A1 | 9/2004 | Dye |
| 2005/0038443 | A1 * | 2/2005 | Hedley et al. ................... 606/91 |
| 2005/0113916 | A1 | 5/2005 | Branch, Jr. |
| 2005/0283245 | A1 | 12/2005 | Gordon et al. |
| 2006/0004376 | A1 * | 1/2006 | Shipp et al. ..................... 606/99 |
| 2006/0122701 | A1 | 6/2006 | Kiester |
| 2006/0200244 | A1 | 9/2006 | Assaker |
| 2006/0229627 | A1 | 10/2006 | Hunt et al. |
| 2006/0241770 | A1 | 10/2006 | Rhoda et al. |
| 2007/0093838 | A1 | 4/2007 | Khodadadyan-Klostermann et al. |
| 2007/0093850 | A1 * | 4/2007 | Harris et al. .................... 606/99 |
| 2007/0225726 | A1 | 9/2007 | Dye et al. |
| 2007/0270968 | A1 | 11/2007 | Baynham et al. |
| 2007/0293869 | A1 | 12/2007 | Conte et al. |
| 2008/0015704 | A1 | 1/2008 | Gradl et al. |
| 2008/0114371 | A1 | 5/2008 | Kluger |
| 2008/0172128 | A1 | 7/2008 | Perez-Cruet et al. |
| 2008/0243126 | A1 | 10/2008 | Gutierrez et al. |
| 2008/0300601 | A1 | 12/2008 | Fabian et al. |
| 2009/0192611 | A1 * | 7/2009 | Lindner ...................... 623/17.11 |
| 2009/0198245 | A1 * | 8/2009 | Phan ................................ 606/99 |
| 2009/0216330 | A1 | 8/2009 | Geisert et al. |
| 2010/0076502 | A1 | 3/2010 | Guyer et al. |
| 2010/0137922 | A1 | 6/2010 | Hunt et al. |
| 2010/0179655 | A1 * | 7/2010 | Hansell et al. ............. 623/17.11 |

FOREIGN PATENT DOCUMENTS

| | | |
|---|---|---|
| EP | 1 532 949 A1 | 5/2005 |
| WO | WO 2004/110251 A2 | 12/2004 |
| WO | WO 2006/047587 A2 | 5/2006 |
| WO | WO 2006/065419 A2 | 6/2006 |
| WO | WO 2009/124269 A1 | 10/2009 |

OTHER PUBLICATIONS

International Search Report; PCT/US2009/039501; Sep. 16, 2009; (7 pages).

* cited by examiner

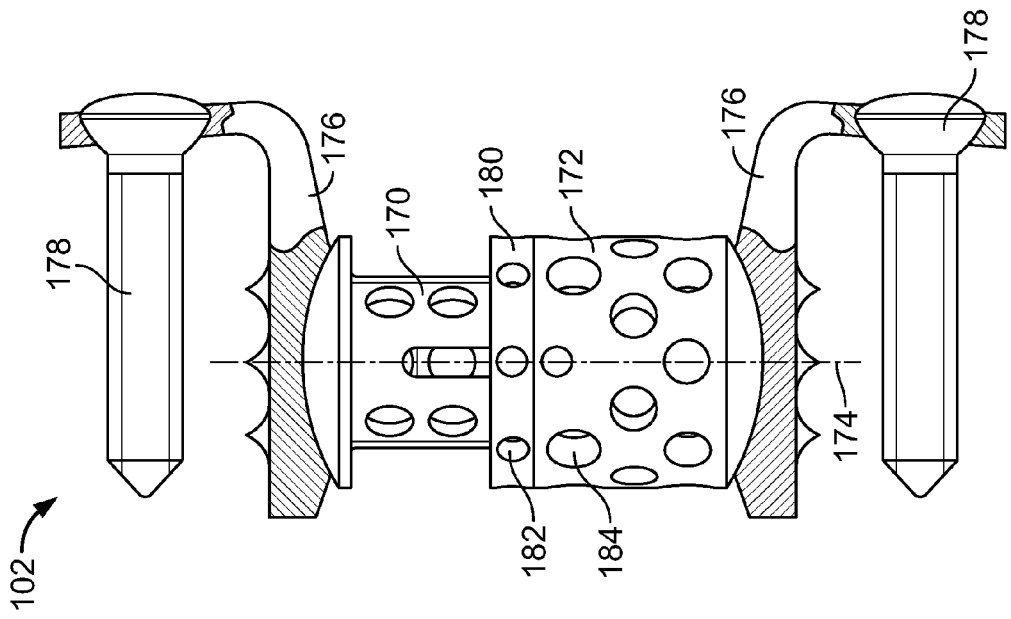
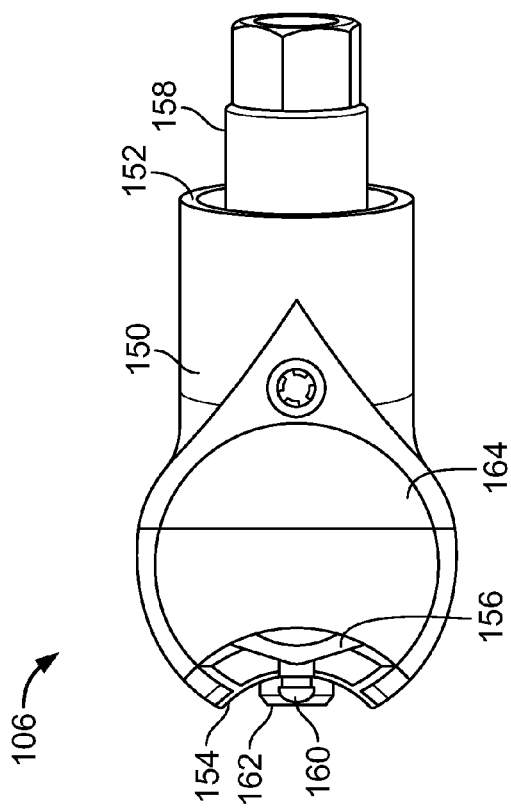

IMPLANT ASSEMBLY HAVING AN ANGLED HEAD

BACKGROUND OF THE INVENTION

The subject matter herein relates generally to implant assemblies, and more particularly, to implant assemblies having angled heads and/or angled handles.

When a vertebrae is broken or crushed, it is frequently necessary to remove the bone partially or completely. In order to prevent the spinal instabilities with damage to the fragile spinal cord and the nerve roots, it is necessary to employ a spacer or implant. The implant bridges the defect vertically between the bodies of the adjacent vertebra and holds them apart at the desired spacing.

The implant is set in an area where the body or bodies of one or more vertebrae have been removed. The length of the implant is then increased by forcing end elements of the implant outward and bringing the outer elements into solid engagement with the confronting vertebral surfaces. The system can be used to distract and to stabilize the vertebrae, as necessary in the event of a destruction of the vertebrae caused by tumor, trauma or infection. The implant can be filled with autologous bone or any other material that ensures that the implant becomes anchored in place in living bone.

Such implants have proven very effective in use. However, it may be fairly difficult to position and expand the implant. Thus, the surgical field must normally be fairly wide in order to permit the surgeon to access the implant with a tool. For example, when placing the implant from the posterior into the anterior part of the spine, the implant is typically desired to be positioned as much in the middle of the spine as possible. Coming from the posterior, the implant is inserted slightly offset to the side and moved around the spine to place the implant in the middle of the anterior part of the vertebral body. Such manipulation of the implant is difficult and requires a large incision through the patient's back in order to achieve the leverage required to position the implant within the spine. A second example is the placement of the implant from the anterior side when manipulation of the implant becomes difficult in a deep situs.

A need remains for an implant assembly capable of positioning an implant from any approach such as the posterior, anterolateral, lateral or anterior of the patient into an anterior part of the spine. A need remains for an implant assembly that can be used with minimal invasion and trauma to the patient.

BRIEF DESCRIPTION OF THE INVENTION

In one embodiment, an implant assembly is provided including an implant having an upper element and a lower element coaxially aligned with one another. The upper and lower elements are configured to be displaced relative to one another along a longitudinal axis of the implant. The implant assembly also includes a setting tool having a cassette and a tool body. The cassette has a housing, a gear held by the housing, and a drive shaft driving the gear. The cassette holds the implant such that the gear engages the implant to displace the upper and lower elements relative to one another. The tool body has an inner portion and an outer portion being angled relative to one another. The cassette is mounted to the inner portion. The tool body has an outer shaft and an inner shaft rotatably received in the outer shaft. The inner shaft includes a flexible joint at the intersection of the inner and outer portions. The inner shaft drives the drive shaft of the cassette.

In another embodiment, an implant assembly is provided including an outer shaft extending along a longitudinal axis between a first end and a second end. The implant assembly also includes an actuator coupled to the second end of the outer shaft. The actuator has a base and a head movable with respect to the base. The base is coupled to the second end and the head is configured to hold a cassette used for setting and distracting an implant. The head is movable with respect to the base to change an angle of orientation of the cassette with respect to the longitudinal axis. The implant assembly also includes an inner shaft rotatably received in the outer shaft. The inner shaft includes a driver coupled to a handle at one end of the driver and coupled to a flexible joint at the other end of the driver. The flexible joint extends through the base and head of the actuator and the flexible joint is configured to transfer the rotation of the driver to the cassette for distracting the implant.

In a further embodiment, a method of setting an implant is provided that includes the step of providing a setting tool, where the setting tool has an outer shaft extending along a longitudinal axis between a first end and a second end and an actuator with a base and a head movable with respect to the base. The base is coupled to the second end and the head is configured to hold a cassette used for setting and distracting an implant. The head being movable with respect to the base to change an angle of orientation of the cassette with respect to the longitudinal axis. The setting tool also has an inner shaft rotatably received in the outer shaft that has a driver coupled to a handle at one end of the driver and coupled to a flexible joint at the other end of the driver that extends through the base and head of the actuator, wherein the flexible joint is configured to transfer the rotation of the driver to the cassette for distracting the implant. The method also includes the steps of attaching an implant to the setting tool, loading the setting tool and implant into the body along the loading axis, actuating the actuator to move the head to an angled position with respect to the base such that the cassette is angled with respect to the longitudinal axis, and rotating the handle to distract the implant to a distracted position.

BRIEF DESCRIPTION OF THE DRAWINGS

FIG. 3 is a top view of a cassette of the implant assembly.

FIG. 4 is a side, partial sectional view of an implant for the implant assembly.

DETAILED DESCRIPTION OF THE INVENTION

Figure 1:
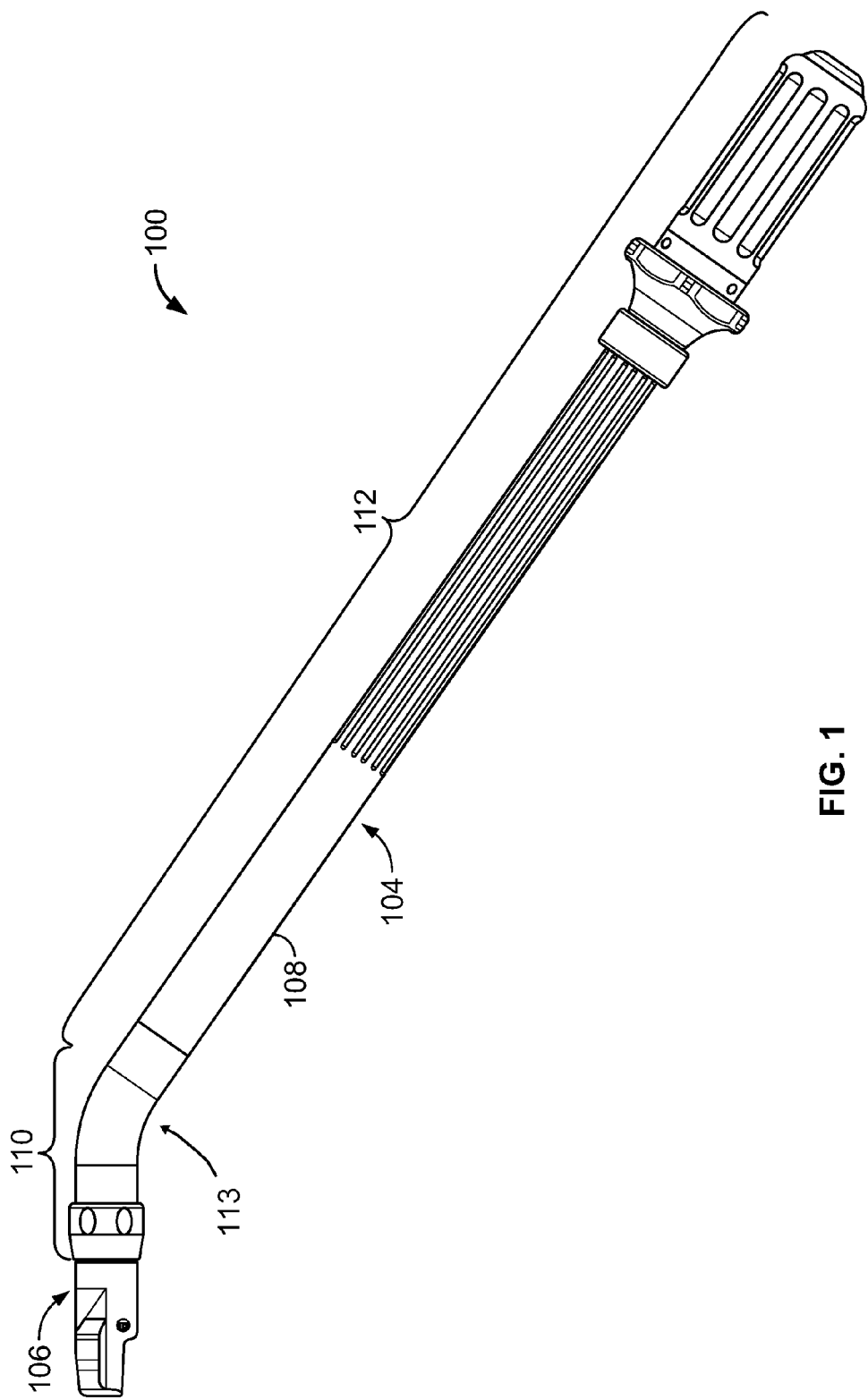
FIG. 1 illustrates an implant assembly formed in accordance with an exemplary embodiment.

FIG. 1 illustrates an implant assembly 100 formed in accordance with an exemplary embodiment. The implant assembly 100 is used for setting and distracting an implant 102 (shown in FIG. 4). In an exemplary embodiment, the implant assembly 100 constitutes a spinal implant assembly configured for setting a spinal implant 102 in place and adjusting the spinal implant 102 between the vertebrae. The implant assembly 100 may be used to set other types of implants in alternative embodiments.

The implant assembly 100 includes a setting tool 104 that is configured to be handled and manipulated by an operator to position the implant 102 within the body and to distract the implant 102 into position within the body. The setting tool 104 includes a cassette 106 at an end thereof that holds the implant 102. The setting tool 104 also includes a tool body 108 that holds the cassette 106. The tool body 108 is held by the operator to move the implant 102 into position within the patient.

The tool body 108 has an inner portion 110 and an outer portion 112 being angled relative to one another. An angled section 113 is provided between the inner and outer portions 110, 112. During use, the inner portion 110 is positioned within the patient and the outer portion 112 extends out of the patient and is held by the operator. The cassette 106 is mounted to an end of the inner portion 110. The tool body 108 is angled so that the implant 102 may be more easily positioned within the patient's body. For example, the implant assembly 100 may be adapted for use in placing the implant 102 from the posterior of the patient's body into an anterior part of the spine. Having the angled tool body 108 allows the cassette 106 to be positioned at the anterior portion of the spine with less angular manipulation of the setting tool 104 as compared to straight setting tools. As such, a smaller incision may be needed and less trauma to the patient may be required to manipulate the cassette 106 into position. The tool body 108 wraps partly around the spine so that cassette 106 and the implant 102 are positioned along the anterior of the spine.

In the illustrated embodiment, the inner portion 110 is relatively short compared to the outer portion 112. The angle or bend in the tool body 108 defines the angular orientation between the inner portion 110 and the outer portion 112. The inner portion 110 extends at an angle that is generally transverse to a longitudinal axis of the outer portion 112. The inner portion 110 may be oriented at any angle with respect to the outer portion 112. In the illustrated embodiment, the inner portion 110 is angled at approximately a 30° angle with respect to the outer portion 112. Other angles are possible in alternative embodiments. Optionally, a family of implant assemblies 100 may be provided, with each member of the family having the inner portion 110 oriented at a different angle with respect to the outer portion 112. For example, each family member may be oriented at 5° increments, such as a 15° member, a 20° member, a 25° member, and so on.

Figure 2:
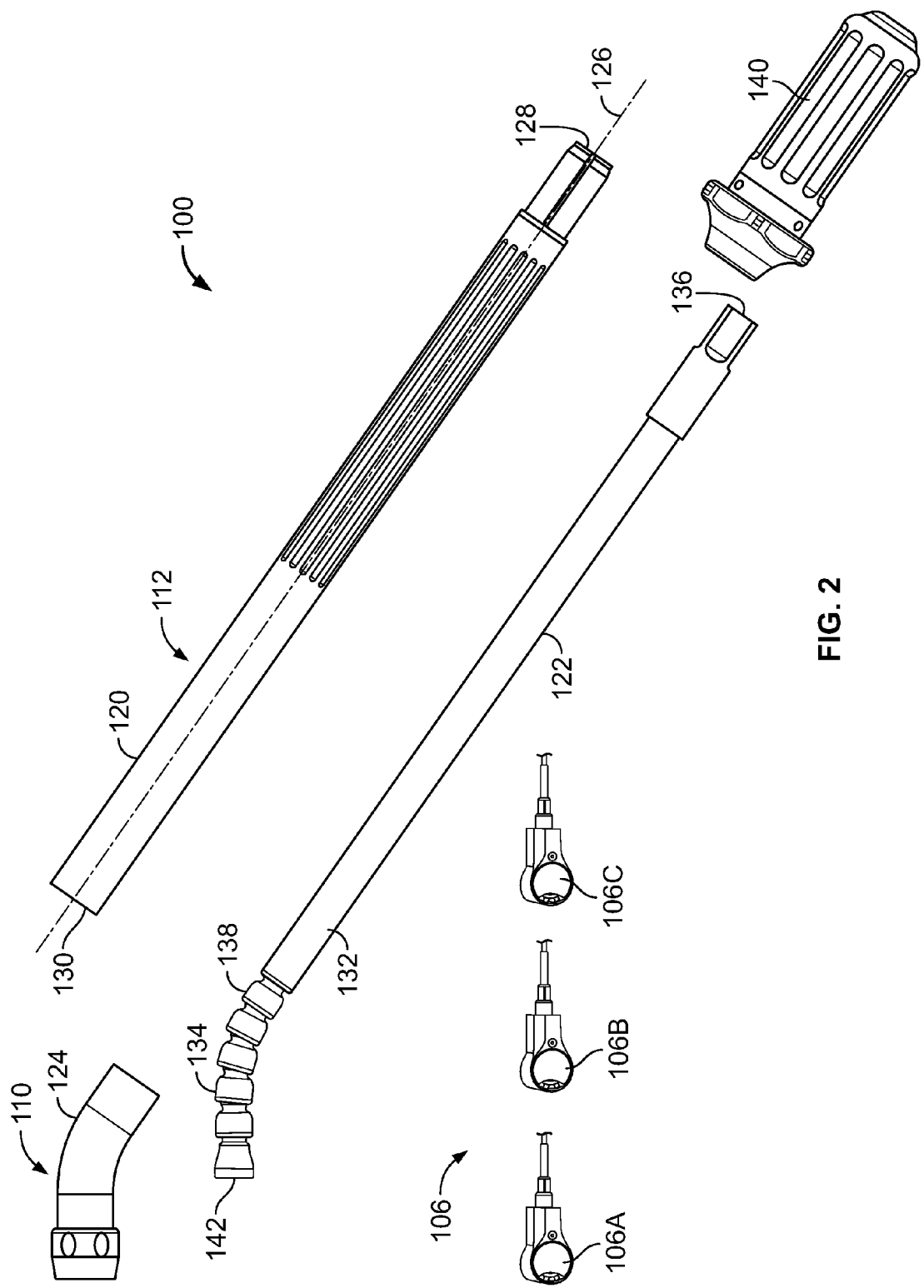
FIG. 2 is an exploded view of the implant assembly shown in FIG. 1.

FIG. 2 is an exploded view of the implant assembly 100. The setting tool 104 includes an outer shaft 120, an inner shaft 122 and a transition shaft 124. The outer shaft 120 extends along a longitudinal axis 126 between a first end 128 and a second end 130. When assembled, the transition shaft 124 is mounted to the second end 130 of the outer shaft 120. The transition shaft 124 includes a bend or curve that defines the angled tool body 108. The outer shaft 120 and the transition shaft 124 are hollow and receive the inner shaft 122. In an exemplary embodiment, the inner shaft 122 is rotatable within the hollow outer shaft and transition shaft 120, 124. The cassette 106 is configured to be coupled to an end of the transition shaft 124 opposite the outer shaft 120.

Optionally, rather than having the outer shaft 120 and the transition shaft 124 separately provided from one another, the outer shaft 120 and transition shaft 124 may be integrally formed with one another. For example, the outer shaft 120 may be curved at the end with the cassette 106 being coupled to the end of the outer shaft 120. Optionally, different types of transition shafts 124 may be utilized with the implant assembly 100. For example, transition shafts 124 having different angles of curvature and/or lengths may each be configured to be selectively mounted to the second end 130 of the outer shaft 120. For example, the transition shafts 124 may be threadably coupled to the second end 130. As such, the setting tool 104 may hold the cassettes 106 at different positions by replacing the transition shaft 124 with a transition shaft 124 having a different angle of curvature or length.

The outer shaft 120 generally defines the outer portion 112 of the tool body 108. The transition shaft 124 generally defines the inner portion 110 of the tool body 108. Optionally, the transition shaft 124 may define a segment of the outer portion 112.

In an exemplary embodiment, the implant assembly 100 may include multiple different cassettes 106, identified in FIG. 2 as cassette 106A, 106B and 106C. The cassettes 106 may be similar to the CS 2256 cassettes commercially available from Ulrich Medical USA, Inc. The cassettes 106 differ from one another in that the cassettes 106 are configured to receive different size implants 102 (shown in FIG. 4). Any number of different types of cassettes 106 may be coupled to the end of the transition shaft 124, and thus be used with the implant assembly 100.

The inner shaft 122 is configured to be rotatably received in the outer shaft 120 and the transition shaft 124. The inner shaft 122 includes a driver 132 and a flexible joint 134 coupled to an end of the driver 132. In an exemplary embodiment, the driver 132 constitutes a rod extending between a first end 136 and a second end 138. The flexible joint 134 is coupled to the second end 138. The driver 132 may be hollow, or alternatively may be solid. Optionally, the first end 136 of the driver 132 may be threaded. A handle 140 is coupled to the first end 136 for rotating the inner shaft 122. For example, the handle 140 may be threaded onto the first end 136. Alternatively, the handle 140 may be attached to the first end 136 by an alternative means. When loaded into the outer shaft 120, the inner shaft 122 may be rotated within the outer shaft 120 by rotating the handle 140. The handle 140 defines an exterior part of the tool body 108. When assembled, the handle 140 is provided at the first end 128 of the outer shaft 120.

The flexible joint 134 constitutes a flexible drive element that is configured to be oriented along a non-linear path. In the illustrated embodiment, the flexible joint 134 includes a plurality of hex adapters 142 arranged in a stacked configuration, with one end of each hex adapter 142 being open to receive an opposite end of another hex adapter 142 therein. The hex adapters 142 are able to be arranged at different angles with respect to other hex adapters 142. The hex adapters 142 hold one another such that, when rotated, the upstream hex adapters 142 (e.g. closer to the driver 132) are able to rotate the downstream hex adapters 142. One of the hex adapters 142 is received in the end 138 of the driver 132. Rotation of the driver 132 causes rotation of the flexible joint 134.

FIG. 3 is a top view of the cassette 106. The cassette 106 includes a housing 150 having a tool end 152 and an implant end 154. The tool end 152 is configured to be mounted to the tool body 108 (shown in FIG. 1). The implant 102 (shown in FIG. 4) is configured to be mounted to the implant end 154.

A gear 156 is held within the housing 150. A drive shaft 158 is also held within the housing 150. The drive shaft 158 is configured to be driven by the inner shaft 122 (shown in FIG. 2). For example, the drive shaft 158 may be coupled to the flexible joint 134 (shown in FIG. 2). Rotation of the flexible joint 134 causes rotation of the drive shaft 158. The drive shaft 158 is operably coupled to the gear 156. Rotation of the drive shaft 158 causes rotation of the gear 156. Optionally, the drive shaft 158 may be rotated along an axis of rotation oriented in a first direction and the gear 156 may be rotated along an axis of rotation that is different than the axis of rotation of the drive shaft 158. Optionally, the axis of rotation of the gear 156 may be perpendicular to the axis of rotation of the drive shaft 158.

The gear 156 includes a plurality of teeth 160 at an outer edge thereof. The teeth 160 are configured to engage the implant 102 to manipulate the implant 102 within the patient's body. In the illustrated embodiment, the teeth 160 constitute posts extending radially outward from the gear 156. The teeth 160 are spaced apart from one another by a predetermined distance along the outer circumference of the gear 156.

In an exemplary embodiment, the cassette 106 includes a set screw 162. The set screw 162 is configured to be coupled to the implant 102 to secure the implant 102 at the implant end 154.

The cassette 106 includes a cover 164 extending along an outer portion of the gear 156. The cover 164 may be secured to the housing 150 to hold the gear 156 within the housing 150. The cover 164 covers the chamber that receives the gear 156.

The cassette 106 illustrated in FIG. 3 constitutes an exemplary embodiment of a cassette for use with the implant assembly 100. The cassette 106 is merely illustrative of one type of cassette that may be used with the implant assembly 100. The implant assembly 100 is not intended to be limited to the cassette 106 shown in FIG. 3. Other types of cassettes may be used in alternative embodiments. Alternative cassettes may have alternative means for holding and/or distracting the implant 102. For example, a cassette having a bevel gear attached to an end of the drive shaft that is rotated about an axis of rotation coincident with the drive shaft may be utilized, such as the bevel gear described in U.S. Pat. No. 6,752,832 to Neumann, the complete subject matter of which is expressly incorporated herein in its entirety. Other types of cassettes may be used in other alternative embodiments.

FIG. 4 is a side, partial sectional view of the implant 102. The implant 102 may be similar to the implant described in U.S. Pat. No. 6,190,413 to Sutcliffe titled Vertebral Implant, the complete subject matter of which is expressly incorporated herein in its entirety. Other types of implants may be used in alternative embodiments, such as the implants described in U.S. Pat. No. 6,752,832, U.S. Pat. No. 6,015,436, U.S. Pat. No. 5,571,192, and the like. The implant 102 illustrated in FIG. 4 constitutes an exemplary embodiment of an implant for use with the implant assembly 100. The implant 102 is merely illustrative of one type of implant that may be used with the implant assembly 100. The implant assembly 100 is not intended to be limited to the implant 102 shown in FIG. 4. Other types of implants may be used in alternative embodiments. Alternative implants may have alternative drive means and/or securing means, which may come in various sizes and diameters. The implants may be configured for use in other parts of the patient's body other than the spine. The implant may be a screw, pin or other orthopedic or medical device that is driven into the patient's body or simply connect to another tool placed within the human body.

The implant 102 includes an upper element 170 and a lower element 172 coaxially aligned with one another along a longitudinal axis 174. The upper and lower elements 170, 172 are configured to be displaced relative to one another along the longitudinal axis 174. As such, the longitudinal length of the implant 102 may be lengthened or shortened once positioned between the vertebrae. Mounting brackets 176 are provided at the ends of the upper and lower elements 170, 172. The mounting brackets may be fastened in each of the vertebrae, such as using the fasteners 178.

In an exemplary embodiment, the implant 102 includes a ring 180 bearing axially on the top end of the lower element 172. The upper element 170 is threaded with an external thread and the ring 180 has an internal thread engaging the external of the upper element 170. Rotation of the ring 180 causes the upper element 170 to move longitudinally with respect to the lower element 172. Once positioned, the upper element 170 and lower element 172 may be locked against relative rotation by the use of a pin or other fixing means. The ring 180 includes a plurality of openings 182 spaced apart along the outer circumference of the ring 180. The openings 182 are configured to receive the teeth 160 of the gear 156 (both shown in FIG. 3). Rotation of the gear 156 causes rotation of the ring 180.

The lower element 172 includes one or more fastening bores 184. The fastening bores 184 may be threaded and are configured to receive the set screw 162 (shown in FIG. 3). When the set screw 162 is secured within the fastening bore 184 the implant 102 is secured to the cassette 106.

In an exemplary embodiment, the upper element 170 and/or lower element 172 include a plurality of openings 186 therethrough. The openings 186 allow the implant 102 to be filled with bone cement and/or bone fragments or other adequate materials to ensure that the implant 102 becomes anchored in place in living bone.

Figure 5:
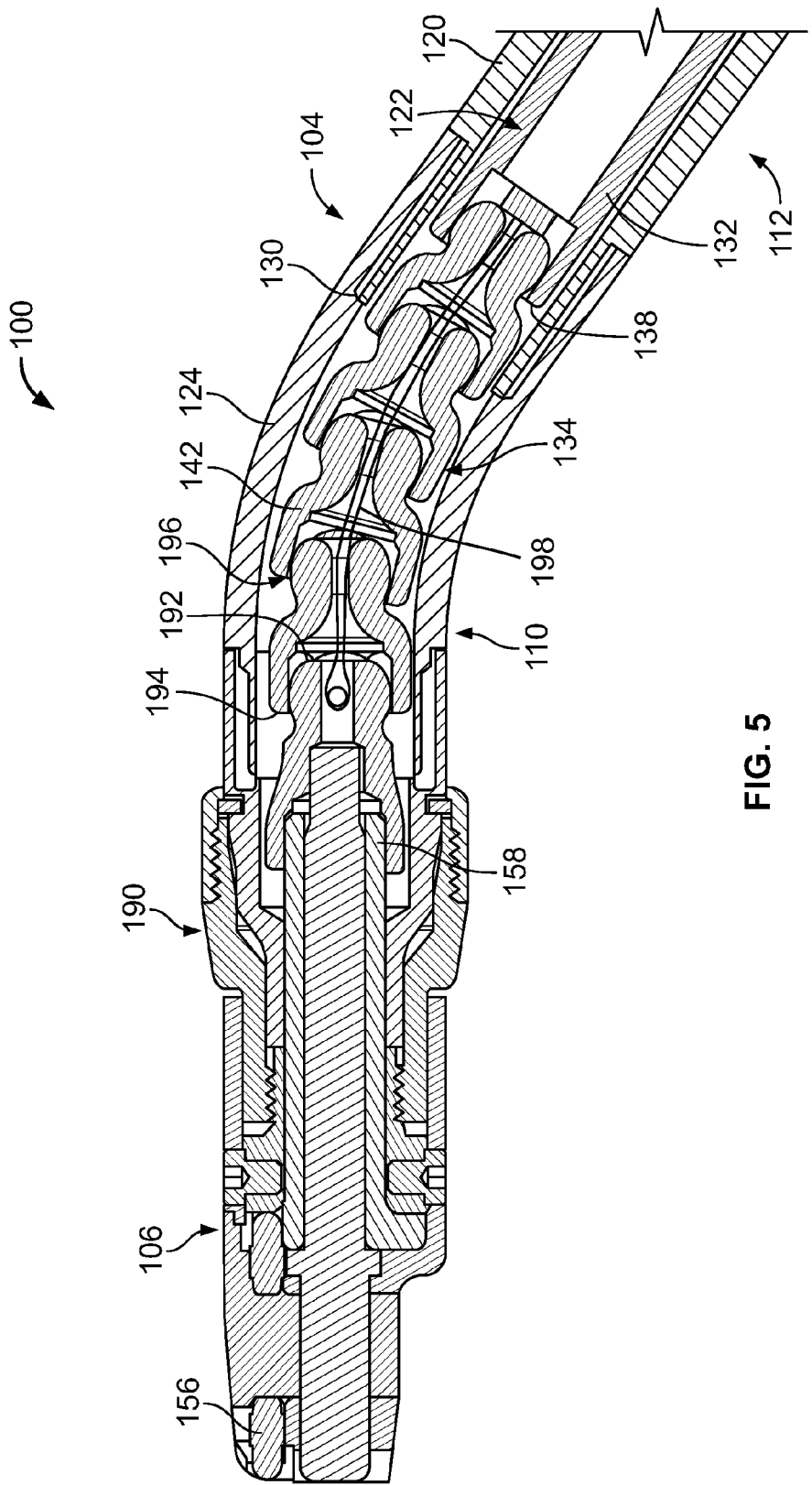
FIG. 5 is a cross-sectional view of a portion of the implant assembly.

FIG. 5 is a cross-sectional view of a portion of the implant assembly 100. FIG. 5 shows the cassette 106 mounted to the inner portion 110 and shows a portion of the outer portion 112. The inner shaft 122 is received in the outer shaft 120 and transition shaft 124. The transition shaft 124 is coupled to the second end 130 of the outer shaft 120. The cassette 106 is coupled to the transition shaft 124 using a threaded coupling 190. The cassette 106 may be secured to the setting tool 104 by an alternative fastener or coupling means in alternative embodiments.

The inner shaft 122 is loaded into the outer shaft 120 such that the second end 138 of the driver 132 is positioned proximate to the second end 130 of the outer shaft 120. The driver 132 receives an end of the flexible joint 134.

In an exemplary embodiment, each hex adapter 142 includes a drive end 192 and a second end 194. The drive end 192 is smaller than the second end 194. The second end 194 includes a hexagonal shaped opening 196 that receives the drive end 192 of an adjacent hex adapter 142. Torque is transferred from one hex adapter 142 to the other when the flexible joint 134 is rotated. The drive end 192 has a bulbous shape allowing the hex adapter 142 to be freely angulated within the opening 196 of the corresponding hex adapter 142. The bulbous shape of the drive end 192 allows for the hex adapter 142 to be positioned within the opening 196 at an angular orientation. The drive end 192 has a hexagonal cross section that corresponds to the hexagon shaped opening 196 and that is tapered at a bottom and a top thereof. Rotation of the hex adapter 142 within the adjacent hex adapter 142 is restricted by the interaction between the drive end 192 and hexagonal shaped opening 196. Additionally, rotation of upstream hex adapters (e.g. hex adapters 142 closer to the driver 132) causes rotation of the downstream hex adapters 142.

The hex adapters 142 are held together by a wire 198. The wire 198 extends through each of the hex adapters 142 and is configured to flex or bend when the flexible joint 134 is bent. The wire 198 may be fixed to the end hex adapters 142 and/or the tool body 108, such as by a pin.

The flexible joint 134 illustrated in FIG. 5 constitutes an exemplary embodiment of a flexible joint for use with the implant assembly 100. The flexible joint 134 is merely illustrative of one type of flexible drive element that may be used with the implant assembly 100. The implant assembly 100 is not intended to be limited to the flexible joint 134 shown in FIG. 5. Other types of flexible drive elements may be used in alternative embodiments that transfer rotation about an axis in one direction to rotation about an axis in a different direction transverse to the other direction.

The cassette 106 is coupled to the setting tool 104 such that the drive shaft 158 of a cassette 106 is configured to be driven by the inner shaft 122. For example, the drive shaft 158 may be loaded into the second end 194 of the downstream-most hex adapter 142 of the flexible joint 134. The flexible joint 134 drives rotation of the drive shaft 158, which drives the gear 156. Alternatively, an extension shaft or intermediate shaft may extend between the flexible joint 134 and the drive shaft 158.

Figure 6:
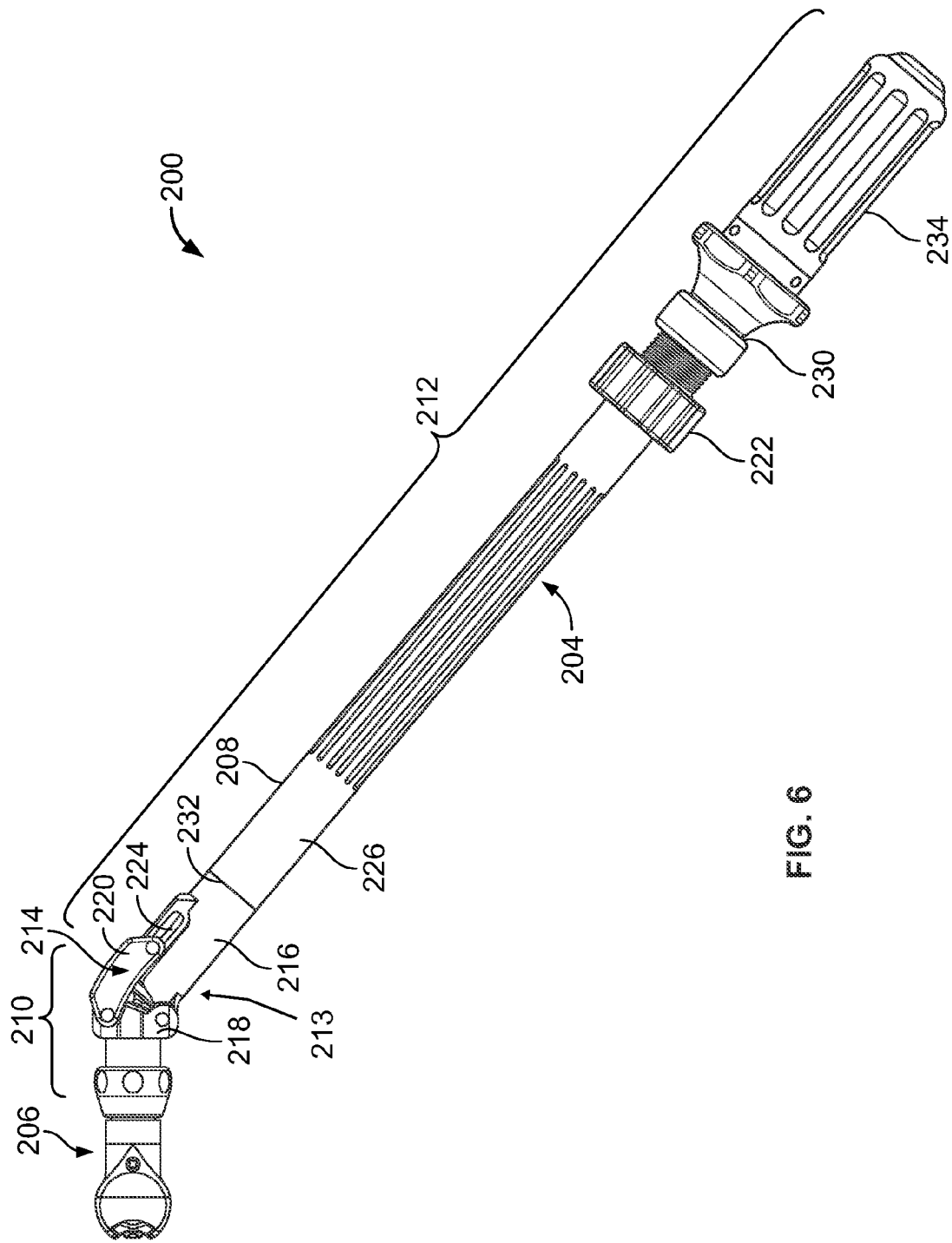
FIG. 6 is a top view of an alternative implant assembly formed in accordance with an alternative embodiment.

FIG. 6 is a top view of an alternative implant assembly 200 having a variable angle head for positioning the implant 102 (shown in FIG. 4). The implant assembly 200 is used for setting the implant 102 by varying the position of the tool head rather than rotating the entire tool into position. The implant assembly 200 is also used for distracting the implant 102 once set in position within the patient.

The implant assembly 200 includes a setting tool 204 that is configured to be handled and manipulated by an operator to position the implant 102 within the body and to distract the implant 102 into position within the body. The setting tool 204 includes a cassette 206 at an end thereof that holds the implant 102 and a tool body 208 that holds the cassette 206. Optionally, the cassette 206 may be substantially similar to the cassette 106 (shown in FIG. 3). Alternatively, a different type of cassette 206 may be held by the setting tool 204. The tool body 208 is held by the operator to move the implant 102 into position within the patient.

The tool body 208 has an inner portion 210 and an outer portion 212 being angled relative to one another. An angled section 213 is provided between the inner and outer portions 210, 212. The inner portion 210 is relatively short compared to the outer portion 212. The angle between the inner portion 210 and the outer portion 212 is variable and may be changed during setting of the implant 102. For example, the inner portion 210 may be pivotably coupled to the outer portion 212. Optionally, the inner portion 210 may be movable between approximately 0° and 45°; however the range of motion may be different in alternative embodiments. For example, the inner portion 210 may have a range of motion of approximately 90°, or even 180° in alternative embodiments. At 0°, the inner portion 210 and the outer portion 212 are in line with one another such that the implant assembly 200 is generally straight.

The implant assembly 200 may be adapted for use in placing the implant 102 from the posterior of the patient's body into an anterior part of the spine. The implant assembly 200 may be initially loaded into the patient's body through an incision with the inner and outer portions 210, 212 at approximately a 0° angle to a certain depth within the patient's body. The inner portion 210 may then be directed partly around the spine so that cassette 206 and the implant 102 are positioned along the anterior of the spine. For example, the inner portion 210 may be actuated to a certain angle, such as a 45° angle with respect to the outer portion 212, allowing the cassette 206 and implant 102 to be positioned at the anterior portion of the spine without having to rotate the setting tool 204 against the patient's body. As such, a smaller incision may be needed and less trauma to the patient may be required to manipulate the cassette 206 into position.

The setting tool 204 includes an actuator 214 between the inner and outer portions 210, 212. The actuator 214 is provided at the angled section 213 and controls the angle between the inner and outer portions 210, 212. The actuator 214 includes a base 216 and a head 218 movable with respect to the base 216. The base 216 is mounted to and/or defines part of the outer portion 212. The head 218 is mounted to and/or defines part of the inner portion 210. In an exemplary embodiment, the head 218 is pivotably coupled to the base 216. A link 220 extends between the base 216 and the head 218. The link 220 is used to actuate the head 218. The link 220 is movable with respect to the base 216 and/or the head 218 to change the angular orientation of the head 218 with respect to the base 216.

In an exemplary embodiment, the setting tool 204 includes a handle 222 that is used to operate the actuator 214. The handle 222 is coupled to the actuator 214 by an element, such as a slide 224 that extends longitudinally between the handle 222 and the link 220. The slide 224 moves longitudinally to control the position of the link 220. For example, as the slide 224 is moved forward, the link 220 pushes one end of the head 218 away from the base 216 to increase the angle of the inner portion 210 with respect to the outer portion 212. As the slide is moved rearward, the link 220 pulls the end of the head 218 toward the base 216 to reduce the angle of the inner portion 210 with respect to the outer portion 212. Optionally, the handle 222 may be rotated, which causes the linear movement of the slide 224. Alternatively, the handle 222 may be translated linearly along the longitudinal axis of the outer portion 212 to move the slide 224.

The setting tool 204 includes an outer shaft 226 and an inner shaft 228 (shown in FIG. 7) held within the outer shaft 226. The outer shaft 226 extends between a first end 230 and a second end 232. The base 216 of the actuator 214 is mounted to the second end 232 of the outer shaft 220. A handle 234 is provided at the first end 230 of the outer shaft 226. The handle 234 is operatively coupled to the inner shaft 228 to rotate the inner shaft 228 within the outer shaft 226. Rotation of the handle 234 is transferred to the cassette 206 by the inner shaft 228. The inner shaft 228 extends through the actuator 214 and includes a flexible drive element that is configured to transfer the rotation from the outer portion 212 to the inner portion 210.

Figure 7:
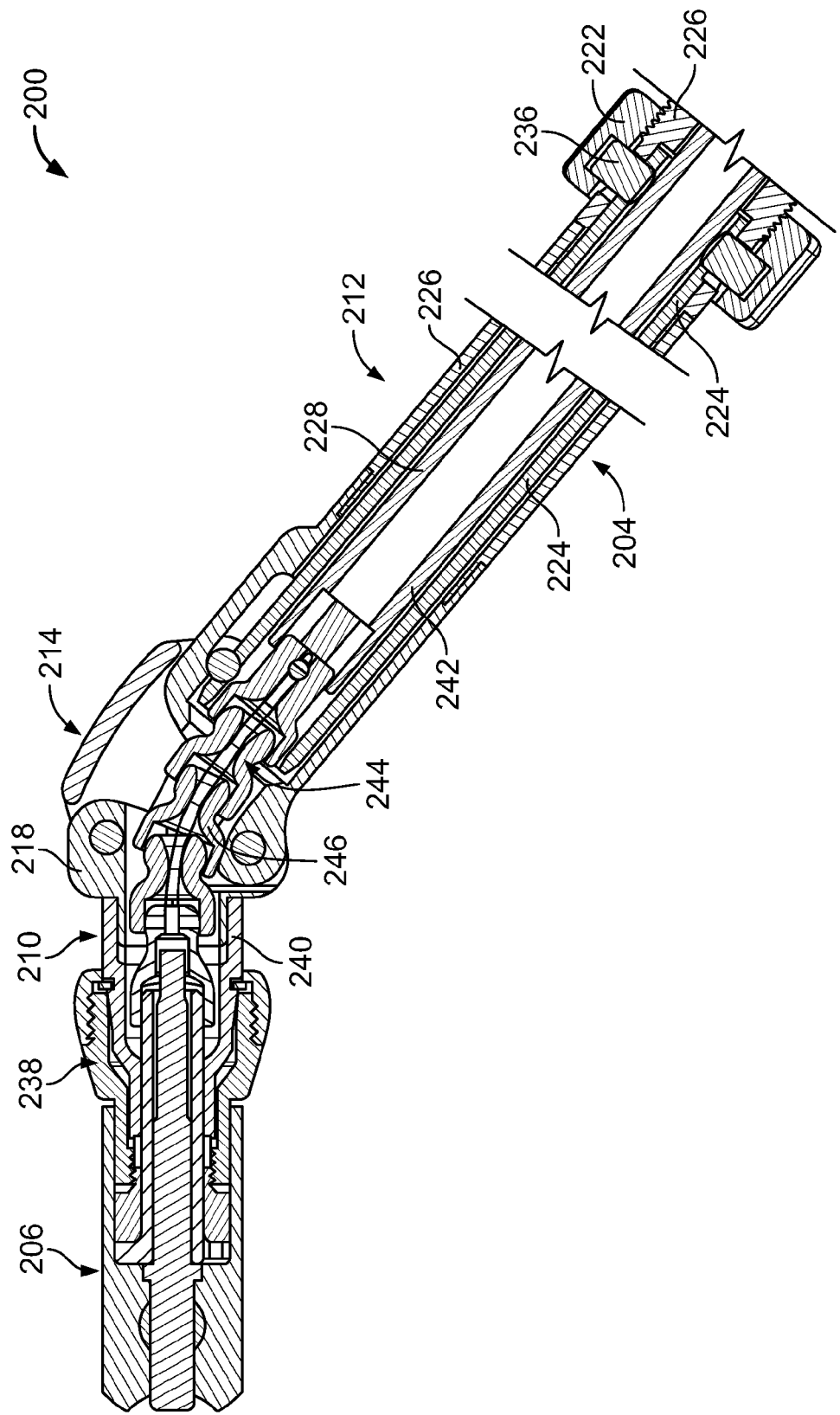
FIG. 7 is a cross-sectional view of a portion of the implant assembly shown in FIG. 6.

FIG. 7 is a cross-sectional view of a portion of the implant assembly 200. FIG. 7 shows the actuator 214 mounted to the outer portion 212 and the cassette 206 mounted to the inner portion 210. FIG. 7 shows the handle 222 attached to the slide 224 and the outer shaft 226. In the illustrated embodiment, the handle 222 is threadably coupled to the outer shaft 226. Rotation of the handle 222 changes the axial position of the handle 222 along the outer shaft 226. The handle 222 is coupled to the slide 224 by a flange 236 extending therebetween. Axial movement of the handle 222 is transferred to the slide 224 by the flange 236.

The slide 224 is received in the hollow tube defined by the outer shaft 226. The slide 224 is movable longitudinally within the outer shaft 226. The slide 224 is a tubular member having a hollow interior. The inner shaft 228 is received in the hollow interior of the slide 224. The inner shaft 228 is rotatable within the slide 224. In an exemplary embodiment, the slide 224 is moved forward and rearward independent of the inner shaft 228, such that the inner shaft 228 does not move longitudinally with the slide 224.

The inner shaft 228 includes a driver 242 and a flexible joint 244 coupled to an end of the driver 242. The driver 242 and flexible joint 244 may be similar to the driver 132 and flexible joint 134 (both shown in FIG. 2). The handle 234 (shown in FIG. 6) is coupled to one end of the driver 242 and the flexible joint 244 is coupled to the other end of the driver 242.

The flexible joint 244 constitutes a flexible drive element that is configured to be oriented along a non-linear path. In the illustrated embodiment, the flexible joint 244 includes a plurality of hex adapters 246 arranged in a stacked configuration. The hex adapters 246 are able to be arranged at different angles with respect to other hex adapters 246. The hex adapters 246 hold one another such that, when rotated, the upstream hex adapters 246 (e.g. closer to the driver 242) are able to rotate the downstream hex adapters 246. One of the hex adapters 246 is received in the end of the driver 242. Rotation of the driver 242 causes rotation of the flexible joint 244.

The cassette 206 is coupled to the inner portion 210 using a threaded coupling 238. Optionally, the coupling 238 may be directly coupled to the head 218 of the actuator 214. Alternatively, a separate outer shaft or extension 240 may be provided between the head 218 and the cassette 206, where the coupling 238 is coupled to the extension 240. The cassette 206 may be secured to the setting tool 204 by an alternative fastener or coupling means in alternative embodiments. The cassette 206 is coupled to the setting tool 204 such that a drive shaft of the cassette 206 is configured to be driven by the inner shaft 228. For example, the drive shaft may be loaded into the downstream-most hex adapter 246 of the flexible joint 244. The flexible joint 244 drives rotation of the drive shaft of the cassette 206.

Figure 8:
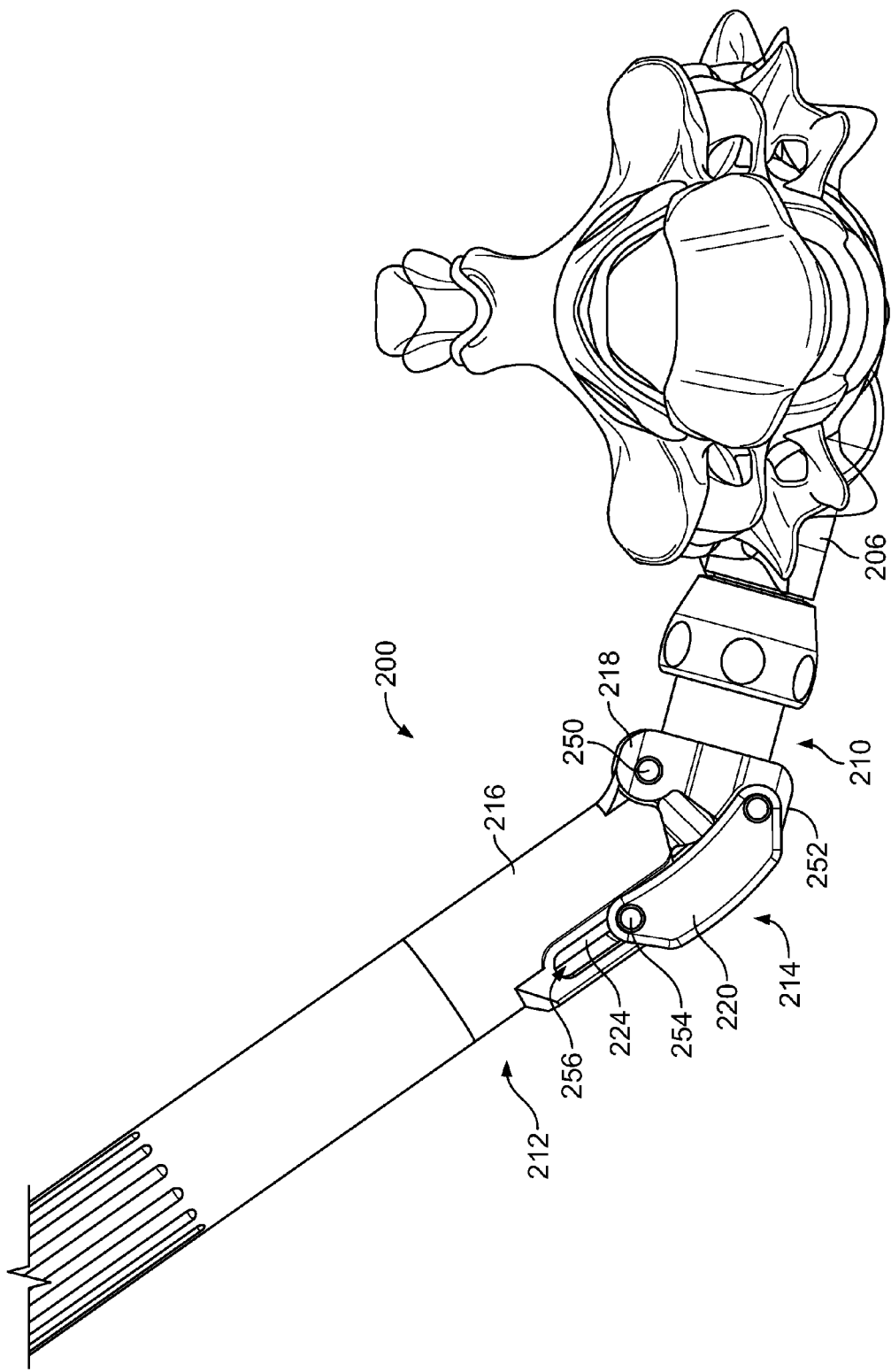
FIG. 8 illustrates the implant assembly shown in FIG. 6 setting an implant between vertebrae of a spine.
Figure 9:
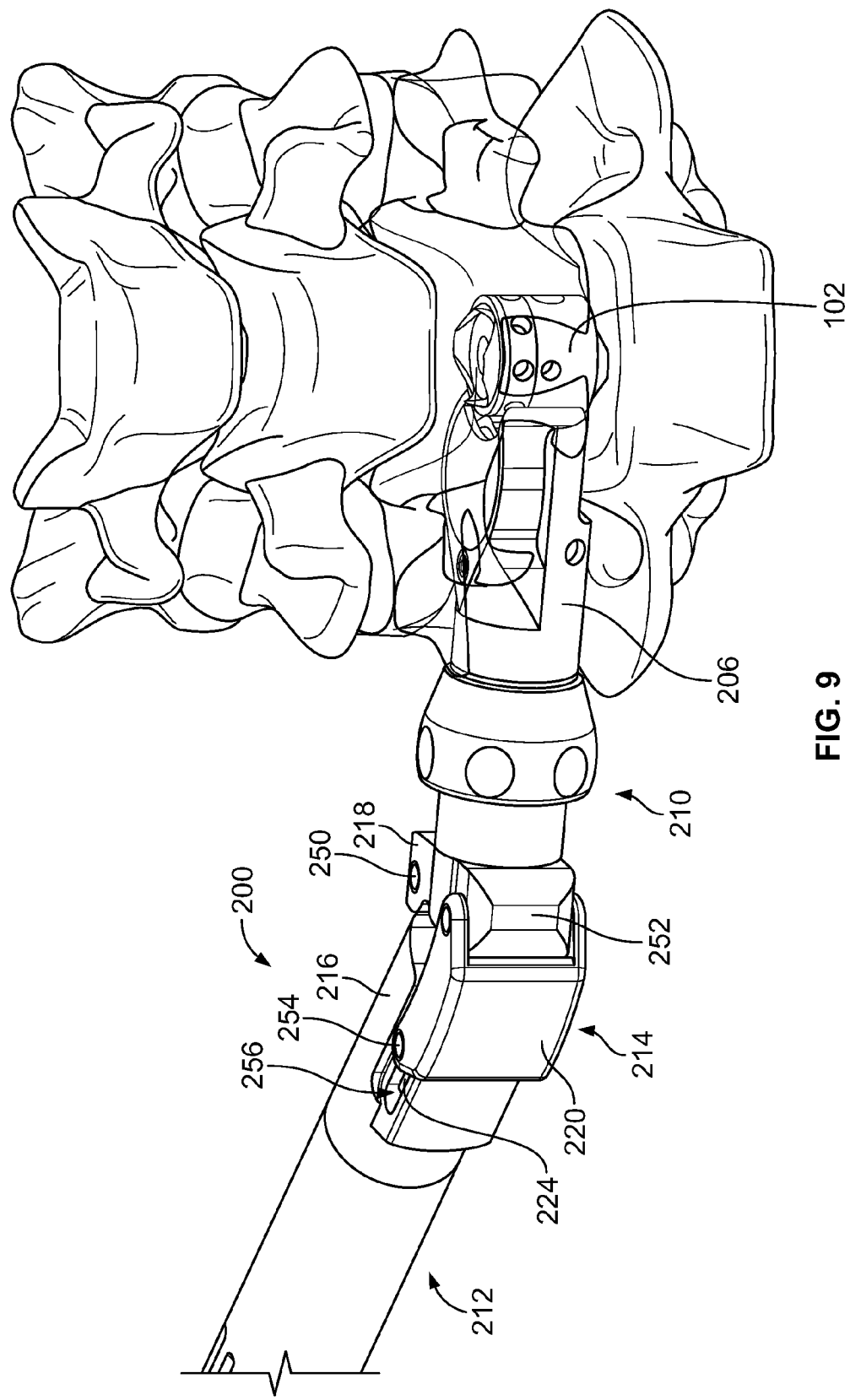
FIG. 9 illustrates the implant assembly shown in FIG. 6 setting an implant between vertebrae of a spine.

FIGS. 8 and 9 illustrate the implant assembly 200 setting an implant 202 between vertebrae of the spine. The implant 202 may be similar to the implant 102. The implant 202 may be set at any location of the spine, such as the thoracic portion, the lumber portion or other portions of the spine. As noted above, the implant assembly 200 may be utilized in applications other than spinal applications, to set and drive other types of implants or implantable devices, including ones that are capable of distraction such as the implant 202 or other types such as screws that are driven into anatomical structures of the patient.

The implant assembly 200 is illustrated with the actuator 214 in an actuated position with the inner portion 210 angled with respect to the outer portion 212. When actuated, the head 218 is pivoted about a pivot pin 250, such that an end 252 of the head 218 is forced away from the base 216. Such movement moves the cassette 206 to an angled position such that the implant 202 is positioned at an anterior position of the spine. The link 220 is coupled to the end 252 and forces the end 252 to move when the slide 224 is actuated. The slide 224 is coupled to the link 220, such as using a set pin 254 or other fastening means. The actuator 214 includes a guide 256 for guiding movement of the set pin 254 along a path. The length of the guide 256 may control the range of motion of the link 220, and thus the angle of the inner portion 210 with respect to the outer portion 212. In the illustrated embodiment, the path is linear; however, the path may be curved in alternative embodiments.

The actuator 214 may be moved from the actuated position to an unactuated position by pulling back on the slide 224, which pulls the set pin 254 back through the guide 256. As the set pin 254 is pulled back, the link 220 moves with the set pin 254 and pulls the end 252 back toward the base 216.

Figure 10:
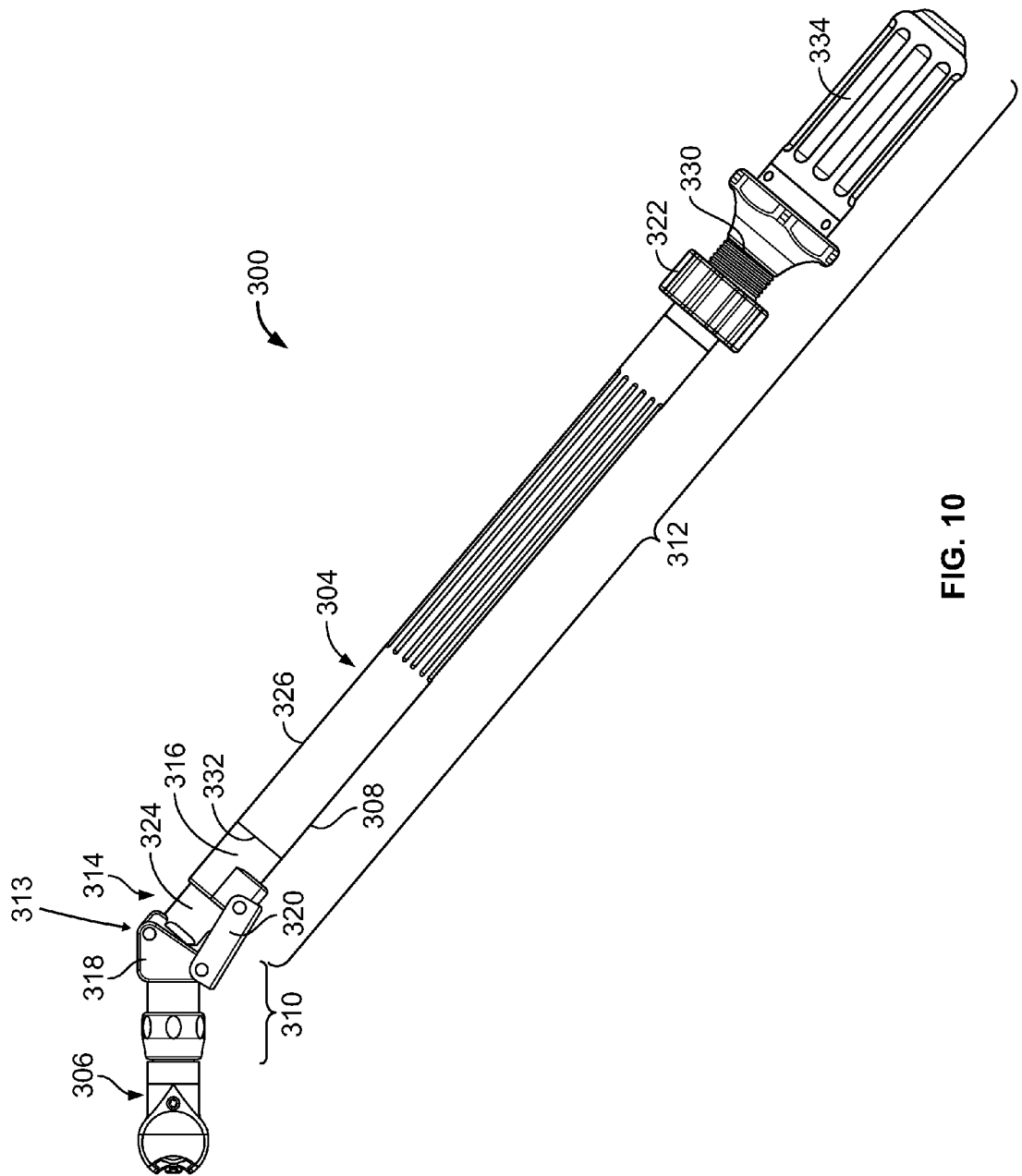
FIG. 10 is a top view of another alternative implant assembly formed in accordance with another alternative embodiment.

FIG. 10 is a top view of an alternative implant assembly 300 having a variable angle head for positioning the implant 102 (shown in FIG. 4). The implant assembly 300 is similar to the implant assembly 200 (shown in FIG. 6); however the implant assembly 300 includes a different actuator 314 as compared to the actuator 214 (shown in FIG. 6). The implant assembly 300 is used for setting the implant 102 by varying the position of the tool head rather than rotating the entire tool into position. The implant assembly 300 is also used for distracting the implant 102 once set in position within the patient.

The implant assembly 300 includes a setting tool 304 that is configured to be handled and manipulated by an operator to position the implant 102 within the body and to distract the implant 102 into position within the body. The setting tool 304 includes a cassette 306 at an end thereof that holds the implant 102 and a tool body 308 that holds the cassette 306. Optionally, the cassette 306 may be substantially similar to the cassette 106 (shown in FIG. 3). Alternatively, a different type of cassette 306 may be held by the setting tool 304. The tool body 308 is held by the operator to move the implant 102 into position within the patient.

The tool body 308 has an inner portion 310 and an outer portion 312 being angled relative to one another. An angled section 313 is provided between the inner and outer portions 310, 312. The inner portion 310 is relatively short compared to the outer portion 312. The angle between the inner portion 310 and the outer portion 312 is variable and may be changed during setting of the implant 102. For example, the inner portion 310 may be pivotably coupled to the outer portion 312. Optionally, the inner portion 310 may be movable between approximately 0° and 45°; however the range of motion may be different in alternative embodiments. At 0°, the inner portion 310 and the outer portion 312 are in line with one another such that the implant assembly 300 is generally straight.

The setting tool 304 includes the actuator 314 between the inner and outer portions 310, 312. The actuator 314 includes a base 316 and a head 318 movable with respect to the base 316. The base 316 is mounted to and/or defines part of the outer portion 312. The head 318 is mounted to and/or defines part of the inner portion 310. In an exemplary embodiment, the head 318 is pivotably coupled to the base 316. A link 320 extends between the base 316 and the head 318. The link 320 is used to hold one side of the head 318 at a predetermined distance from the base 316, while the opposite side of the head 318 is freely movable with respect to the base 316. The head 318 is movable with respect to the base 316 to change the angular orientation of the head 318 with respect to the base 316.

In an exemplary embodiment, the setting tool 304 includes a handle 322 that is used to operate the actuator 314. The handle 322 is coupled to the actuator 314 by an element, such as a slide 324 that extends longitudinally between the handle 322 and the head 318. The slide 324 moves longitudinally to control the position of the head 318. For example, as the slide 324 is moved forward, one side of the head 318 is pushed away from the base 316, while the link 320 holds the other end from moving with respect to the base 316, to increase the angle of the inner portion 310 with respect to the outer portion 312. As the slide 324 is moved rearward, the slide 324 pulls the side of the head 318 toward the base 316 to reduce the angle of the inner portion 310 with respect to the outer portion 312. Optionally, the handle 322 may be rotated, which causes the linear movement of the slide 324. Alternatively, the handle 322 may be translated linearly along the longitudinal axis of the outer portion 312 to move the slide 324.

The setting tool 304 includes an outer shaft 326 and an inner shaft 328 (shown in FIG. 11) held within the outer shaft 326. The outer shall 326 extends between a first end 330 and a second end 332. The base 316 of the actuator 314 is mounted to the second end 332 of the outer shaft 320. A handle 334 is provided at the first end 330 of the outer shaft 326. The handle 334 is operatively coupled to the inner shaft 328 to rotate the inner shaft 328 within the outer shaft 326. Rotation of the handle 334 is transferred to the cassette 306 by the inner shaft 328. The inner shaft 328 extends through the actuator 314 and includes a flexible drive element that is configured to transfer the rotation from the outer portion 312 to the inner portion 310.

Figure 11:
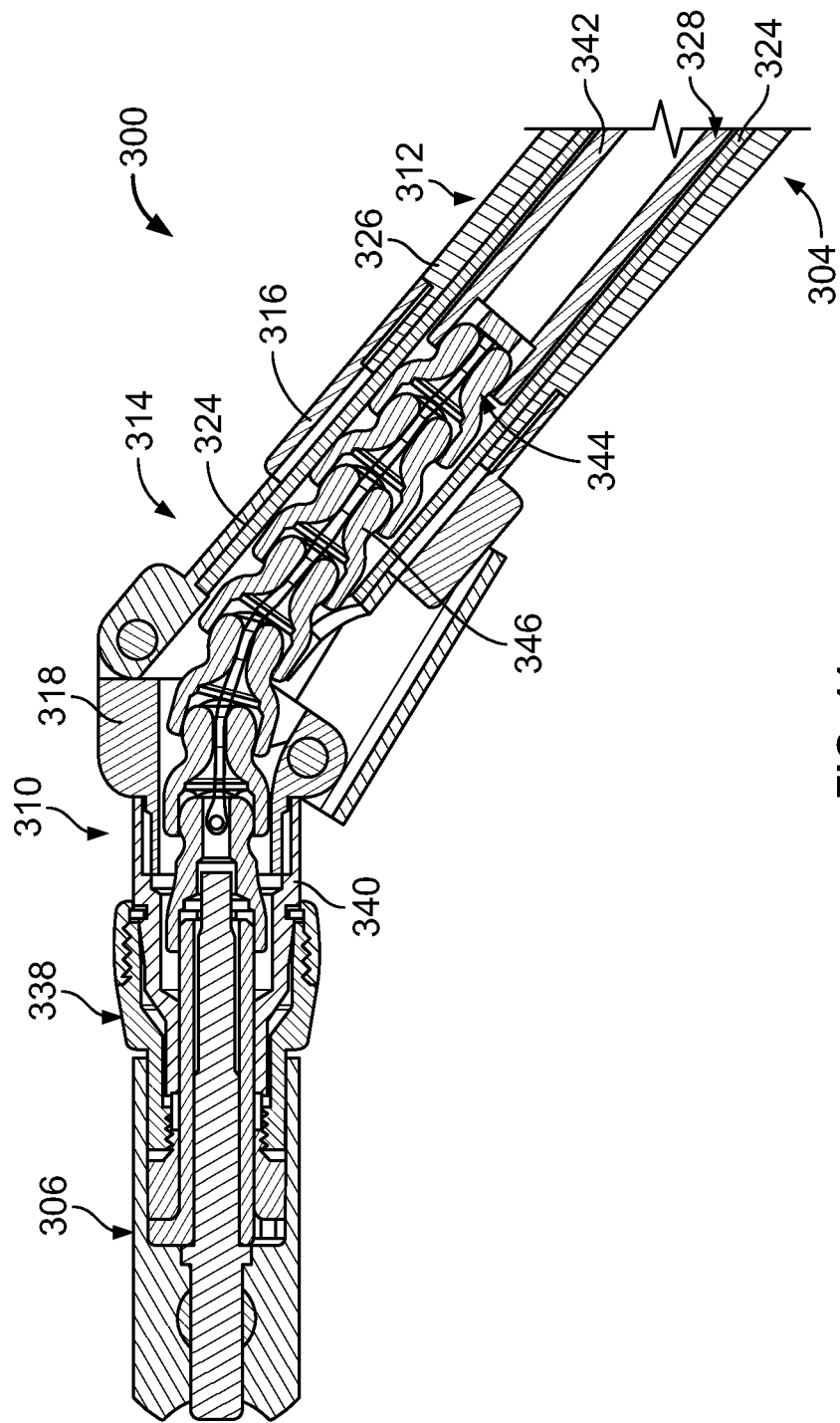
FIG. 11 is a cross-sectional view of a portion of the implant assembly shown in FIG. 10.

FIG. 11 is a cross-sectional view of a portion of the implant assembly 300. FIG. 11 shows the actuator 314 mounted to the outer portion 312 and the cassette 306 mounted to the inner portion 310.

The slide 324 is received in the hollow tube defined by the outer shaft 326. The slide 324 may be coupled to the handle 322 (shown in FIG. 10) in a similar manner as the slide 224 being coupled to the handle 222 (both shown in FIG. 7). The slide 324 is movable longitudinally within the outer shaft 326. The slide 324 is a tubular member having a hollow interior. The inner shaft 328 is received in the hollow interior of the slide 324. The inner shaft 328 is rotatable within the slide 324. In an exemplary embodiment, the slide 324 is moved forward and rearward independent of the inner shaft 328, such that the inner shaft 328 does not move longitudinally with the slide 324.

The inner shaft 328 includes a driver 342 and a flexible joint 344 coupled to an end of the driver 342. The driver 342 and flexible joint 344 may be similar to the driver 132 and flexible joint 134 (both shown in FIG. 3). The handle 334 (shown in FIG. 10) is coupled to one end of the driver 342 and the flexible joint 344 is coupled to the other end of the driver 342.

The flexible joint 344 constitutes a flexible drive element that is configured to be oriented along a non-linear path. In the illustrated embodiment, the flexible joint 344 includes a plurality of hex adapters 346 arranged in a stacked configuration. The hex adapters 346 are able to be arranged at different angles with respect to other hex adapters 346. The hex adapters 346 hold one another such that, when rotated, the upstream hex adapters 346 (e.g. closer to the driver 342) are able to rotate the downstream hex adapters 346. One of the hex adapters 346 is received in the end of the driver 342. Rotation of the driver 342 causes rotation of the flexible joint 344.

The cassette 306 is coupled to the inner portion 310 using a threaded coupling 338. Optionally, the coupling 338 may be directly coupled to the head 318 of the actuator 314. Alternatively, a separate outer shaft or extension 340 may be provided between the head 318 and the cassette 306, where the coupling 338 is coupled to the extension 340. The cassette 306 may be secured to the setting tool 304 by an alternative fastener or coupling means in alternative embodiments. The cassette 306 is coupled to the setting tool 304 such that a drive shaft of the cassette 306 is configured to be driven by the inner shaft 328. For example, the drive shaft may be loaded into the downstream-most hex adapter 346 of the flexible joint 344. The flexible joint 344 drives rotation of the drive shaft of the cassette 306.

Figure 12:
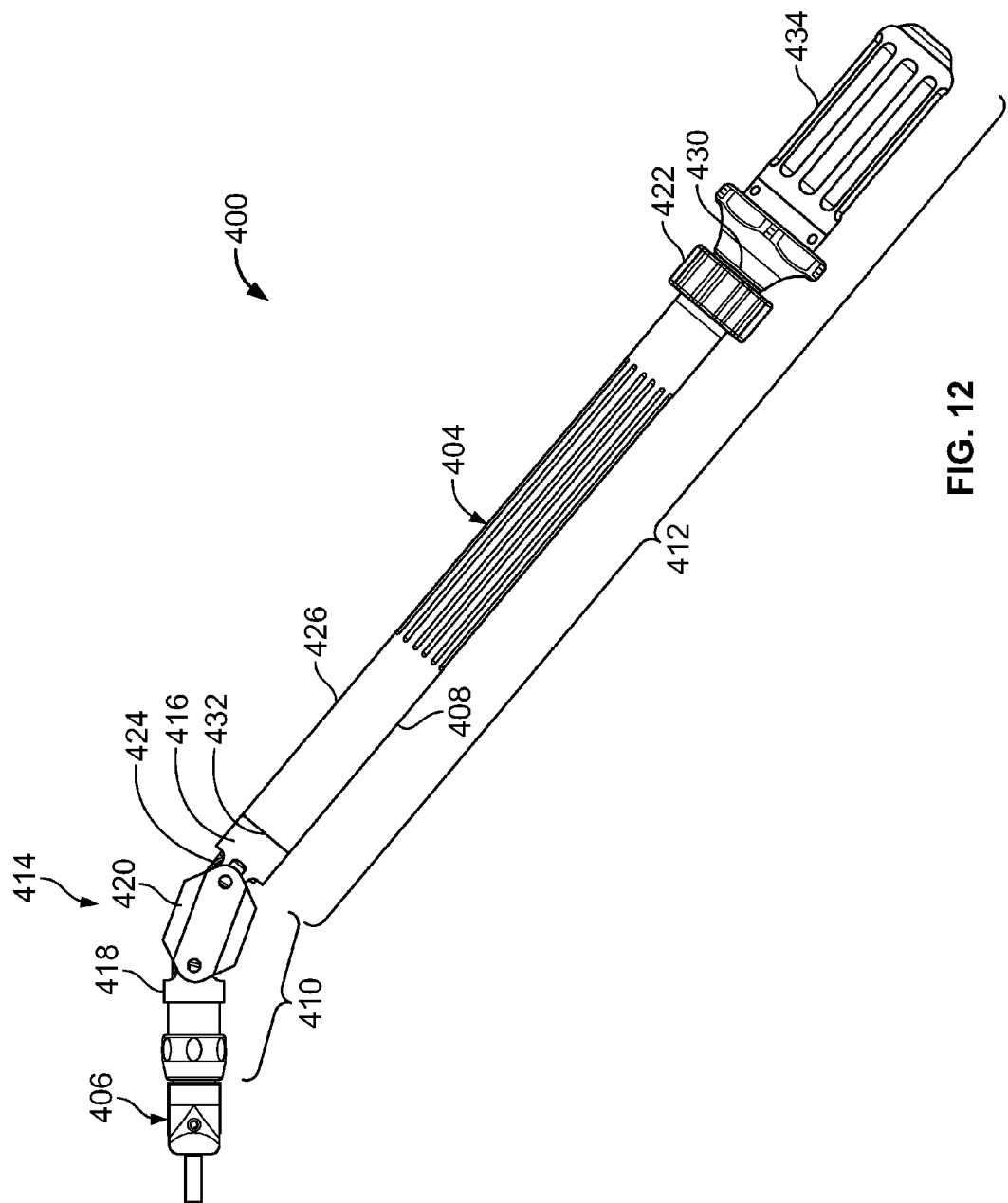
FIG. 12 is a top view of a further alternative implant assembly formed in accordance with a further alternative embodiment.

FIG. 12 is a top view of an alternative implant assembly 400 having a variable angle head for positioning the implant 102 (shown in FIG. 4). The implant assembly 400 is similar to the implant assembly 200 (shown in FIG. 6); however the implant assembly 400 includes a different actuator 414 as compared to the actuator 214 (shown in FIG. 6). The implant assembly 400 is used for setting the implant 102 by varying the position of the tool head rather than rotating the entire tool into position. The implant assembly 400 is also used for distracting the implant 102 once set in position within the patient.

The implant assembly 400 includes a setting tool 404 that is configured to be handled and manipulated by an operator to position an implant 405 within the body and to drive the implant 405 into an anatomical structure of the patient. The setting tool 404 includes a drive 406 at an end thereof that holds the implant 405 and a tool body 408 that holds the drive 406. The drive 406 may have a particular head for driving the implant 405, which may be a screw or other type of implantable device. The drive 406 may have a particular shape depending on the type of implantable device. In an alternative embodiment, a cassette, substantially similar to the cassette 106 (shown in FIG. 4), may be attached to the implant assembly 400. The tool body 408 is held by the operator to move the implant 102 into position within the patient.

The tool body 408 has an inner portion 410 and an outer portion 412 being angled relative to one another. An angled section 413 is provided between the inner and outer portions 410, 412. The inner portion 410 is relatively short compared to the outer portion 412. The angle between the inner portion 410 and the outer portion 412 is variable and may be changed during setting of the implant 102. For example, the inner portion 410 may be pivotably coupled to the outer portion 412. Optionally, the inner portion 410 may be movable between approximately 0° and 45°; however the range of motion may be different in alternative embodiments. At 0°, the inner portion 410 and the outer portion 412 are in line with one another such that the implant assembly 400 is generally straight.

The setting tool 404 includes the actuator 414 between the inner and outer portions 410, 412. The actuator 414 includes a base 416 and a head 418 movable with respect to the base 416. The base 416 is mounted to and/or defines part of the outer portion 412. The head 418 is mounted to and/or defines part of the inner portion 410. The head 418 is movable with respect to the base 416 to change the angular orientation of the head 418 with respect to the base 416. A link 420 extends between the base 416 and the head 418. In an exemplary embodiment, one end of the link 420 is pivotably coupled to the base 416 and the opposite end of the link 420 is pivotably coupled to the head 418.

In an exemplary embodiment, the setting tool 404 includes a handle 422 that is used to operate the actuator 414. The handle 422 is coupled to the actuator 414 by an element, such as a slide 424 (shown in FIG. 13) that extends longitudinally between the handle 422 and the head 418. Optionally, the handle 422 may be rotated, which causes the linear movement of the slide 424. Alternatively, the handle 422 may be translated linearly along the longitudinal axis of the outer portion 412 to move the slide 424.

The setting tool 404 includes an outer shaft 426 and an inner shaft 428 (shown in FIG. 13) held within the outer shaft 426. The outer shall 426 extends between a first end 430 and a second end 432. The base 416 of the actuator 414 is mounted to the second end 432 of the outer shaft 426. A handle 434 is provided at the first end 430 of the outer shaft 426. The handle 434 is operatively coupled to the inner shaft 428 to rotate the inner shaft 428 within the outer shaft 426. Rotation of the handle 434 is transferred to the drive 406 by the inner shaft 428. The inner shaft 428 extends through the actuator 414 and includes a flexible drive element that is configured to transfer the rotation from the outer portion 412 to the inner portion 410.

Figure 13:
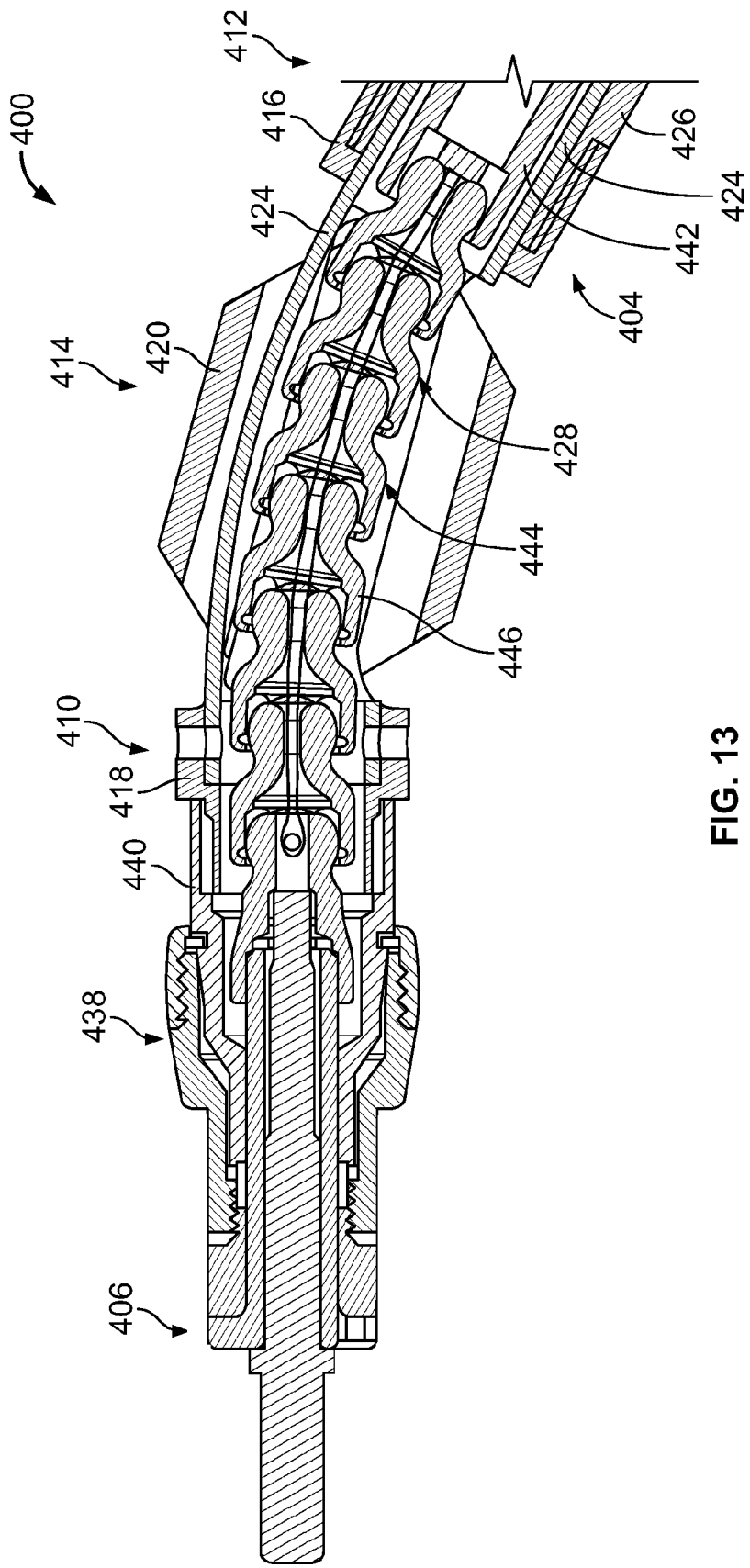
FIG. 13 is a cross-sectional view of a portion of the implant assembly shown in FIG. 12.

FIG. 13 is a cross-sectional view of a portion of the implant assembly 400. FIG. 7 shows the actuator 414 mounted to the outer portion 412 and the drive 406 mounted to the inner portion 410.

The slide 424 is received in the hollow tube defined by the outer shaft 426. The slide 424 may be coupled to the handle 422 (shown in FIG. 12) in a similar manner as the slide 224 being coupled to the handle 222 (both shown in FIG. 7). The slide 424 is movable longitudinally within the outer shaft 426 to control the position of the head 418. For example, as the slide 424 is moved forward, one side of the head 418 is pushed forward away from the base 416. The base 416 and the head 418 are pivoted about the link 420 to increase the angle of the inner portion 410 with respect to the outer portion 412. As the slide 424 is moved rearward, the slide 424 pulls the side of the head 418 back toward the base 416 to reduce the angle of the inner portion 410 with respect to the outer portion 412.

The slide 424 is a tubular member having a hollow interior. The inner shaft 428 is received in the hollow interior of the slide 424. The inner shaft 428 is rotatable within the slide 424. In an exemplary embodiment, the slide 424 is moved forward and rearward independent of the inner shaft 428, such that the inner shaft 428 does not move longitudinally with the slide 424.

The inner shaft 428 includes a driver 442 and a flexible joint 444 coupled to an end of the driver 442. The driver 442 and flexible joint 444 may be similar to the driver 132 and flexible joint 134 (both shown in FIG. 4). The handle 434 (shown in FIG. 12) is coupled to one end of the driver 442 and the flexible joint 444 is coupled to the other end of the driver 442.

The flexible joint 444 constitutes a flexible drive element that is configured to be oriented along a non-linear path. In the illustrated embodiment, the flexible joint 444 includes a plurality of hex adapters 446 arranged in a stacked configuration. The hex adapters 446 are able to be arranged at different angles with respect to other hex adapters 446. The hex adapters 446 hold one another such that, when rotated, the upstream hex adapters 446 (e.g. closer to the driver 442) are able to rotate the downstream hex adapters 446. One of the hex adapters 446 is received in the end of the driver 442. Rotation of the driver 442 causes rotation of the flexible joint 444.

The drive 406 is coupled to the inner portion 410 using a threaded coupling 438. Optionally, the coupling 438 may be directly coupled to the head 418 of the actuator 414. Alternatively, a separate outer shaft or extension 440 may be provided between the head 418 and the drive 406, where the coupling 438 is coupled to the extension 440. The drive 406 may be secured to the setting tool 404 by an alternative fastener or coupling means in alternative embodiments. The drive 406 is coupled to the setting tool 404 such that a drive shaft of the drive 406 is configured to be driven by the inner shaft 428. For example, the drive shaft may be loaded into the downstream-most hex adapter 446 of the flexible joint 444. The flexible joint 444 drives rotation of the drive shaft of the drive 406.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. An implant assembly comprising:
a tool body having an implant end and an outer end opposite the implant end, the implant end being configured to be positioned in a patient, the outer end being configured to be held by a user outside of the patient, the tool body having an inner portion at the implant end and an outer portion at the outer end with an angled section between the inner and outer portions, the angled section angling the inner and outer portions relative to one another, the tool body comprising an actuator separately manufactured from, and coupled to, the inner and outer portions of the tool body, the actuator being configured to vary the angular orientation of the inner portion with respect to the outer portion while the tool body is located within a patient;
an inner shaft rotatably received in the tool body, the inner shaft having a flexible joint extending through the angled section between a drive end and a second end, the flexible joint being rotatable within the angled section, wherein the flexible joint comprises a plurality of hex adapters having hexagon shaped openings that receive a drive end of another hex adapter, the drive end having a plurality of flats that engage the flats of the corresponding hexagon shaped opening, the hex adapters being configured to be positioned at a plurality of angles within the corresponding opening of the adjacent hex adapter, the inner shaft comprising a driver extending through the outer portion of the tool body and being coupled to the drive end of the flexible joint, wherein the flexible joint is configured to transfer rotation of the driver to the second end of the flexible joint; and
a handle coupled to the driver for rotating the driver within the tool body.

2. The implant assembly of claim 1, wherein the actuator is located between the inner and outer portions at the angled section, the actuator varying the angular orientation of the inner portion with respect to the outer portion.

3. The implant assembly of claim 1, wherein the flexible joint constitutes a flexible drive element configured to be oriented along a non-linear path.

4. The implant assembly of claim 1, further comprising a cassette removably coupled to an end of the inner portion of the tool body, the cassette having a housing, a gear held by the housing, and a drive shaft driving the gear, the drive shaft being driven by the flexible joint.

5. The implant assembly of claim 4, further comprising an implant held by the cassette, the implant comprising an upper element and a lower element coaxially aligned with one another, the upper and lower elements being configured to be displaced relative to one another along a longitudinal axis of the implant by the gear.

6. The implant assembly of claim 1, wherein the inner portion includes an attachment end facing the outer portion at the angled section and the inner portion includes a cassette end opposite the attachment end, the implant assembly further comprising a cassette removably coupled to the cassette end of the inner portion of the tool body, the cassette having a housing, a gear held by the housing, and a drive shaft driving the gear, the drive shaft being driven by the flexible joint.

7. The implant assembly of claim 1, wherein the inner portion includes an attachment end facing the outer portion at the angled section and the inner portion includes a cassette end opposite the attachment end, the implant assembly further comprising a cassette threadably coupled to the cassette end of the inner portion of the tool body such that the cassette is configured to be removed and replaced by a different cassette, the cassette having a housing, a gear held by the housing, and a drive shaft driving the gear, the drive shaft being driven by the flexible joint.

8. The implant assembly of claim 1, wherein the actuator is located between the inner and outer portions, the actuator comprises a link extending between a base and a head, the base coupled to the outer portion and the head coupled to the inner portion, the head being coupled to the base at a pivot pin, the head being rotated about the pivot pin to change an angular orientation of the head with respect to the base.

9. The implant assembly of claim 1, wherein the actuator is located between the inner and outer portions, the actuator comprises a link extending between a base and a head, the base coupled to the outer portion and the head coupled to the inner portion, the head being coupled to a slide that extends longitudinally between the handle and the link, the slide moving longitudinally to control the position of the head relative to the base to change the angle of the inner portion with respect to the outer portion.

10. The implant assembly of claim 1, wherein the tool body extends along a tool axis, the handle, outer portion and inner portion being generally aligned along the tool axis with the inner portion being provided at a distal end of the tool body, the handle being provided at a proximal end of the tool axis, the outer portion being provided between the handle and the inner portion.

11. An implant assembly comprising:
a tool body having an implant end and an outer end opposite the implant end, the implant end being configured to be positioned in a patient, the outer end being configured to be held by a user outside of the patient, the tool body having an inner portion at the implant end and an outer portion at the outer end with an angled section between the inner and outer portions, the angled section angling the inner and outer portions relative to one another, the tool body comprising an actuator separately manufactured from, and coupled to, the inner and outer portions of the tool body, wherein the actuator is located between the inner and outer portions, the actuator comprises a link extending between a base and a head, the base coupled to the outer portion and the head coupled to the inner portion, the link being movable with respect to the head and the base to change an angular orientation of the head with respect to the base, the actuator being configured to vary the angular orientation of the inner portion with respect to the outer portion while the tool body is located within a patient;
an inner shaft rotatably received in the tool body, the inner shaft having a flexible joint extending through the angled section between a drive end and a second end, the flexible joint being rotatable within the angled section, the inner shaft comprising a driver extending through the outer portion of the tool body and being coupled to the drive end of the flexible joint, wherein the flexible joint is configured to transfer rotation of the driver to the second end of the flexible joint; and
a handle coupled to the driver for rotating the driver within the tool body.

12. The implant assembly of claim 11, wherein the flexible joint comprises a plurality of hex adapters having hexagon shaped openings that receive a drive end of another hex adapter, the drive end having a plurality of flats that engage the flats of the hexagon shaped opening, the hex adapters being configured to be positioned at a plurality of angles within the corresponding opening of the adjacent hex adapter.

13. The implant assembly of claim 11, further comprising a cassette removably coupled to an end of the inner portion of the tool body, the cassette having a housing, a gear held by the housing, and a drive shaft driving the gear, the drive shaft being driven by the flexible joint.

14. The implant assembly of claim 11, wherein the head is coupled to the base at a pivot pin, the head being rotated about the pivot pin to change an angular orientation of the head with respect to the base.

15. The implant assembly of claim 11, wherein the head is coupled to a slide that extends longitudinally between the handle and the link, the slide moving longitudinally to control the position of the head relative to the base to change the angle of the inner portion with respect to the outer portion.

16. The implant assembly of claim 11, wherein the tool body extends along a tool axis, the handle, outer portion and inner portion being generally aligned along the tool axis with the inner portion being provided at a distal end of the tool body, the handle being provided at a proximal end of the tool axis, the outer portion being provided between the handle and the inner portion.

17. An implant assembly comprising:
an implant configured to be located within a patient, the implant comprising an upper element and a lower element coaxially aligned with one another, the upper and lower elements being configured to be displaced relative to one another along a longitudinal axis of the implant; and
a setting tool comprising:
a cassette having a housing, a gear held by the housing, and a drive shaft driving the gear, the cassette holding the implant such that the gear engages the implant to displace the upper and lower elements relative to one another; and
a tool body having an implant end and an outer end opposite the implant end, the implant end being configured to be implanted in a patient, the outer end being configured to be held by a user outside of the patient, the tool body having an inner portion at the implant end and an outer portion at the outer end with an angled section between the inner and outer portions, the angled section angling the inner and outer portions relative to one another, the angular orientation of the inner portion with respect to the outer portion being variable, the tool body comprising an actuator separately manufactured from, and coupled to, the inner and outer portions of the tool body, the actuator is configured to vary the angular orientation of the inner portion and cassette with respect to the outer portion while the tool body is located within a patient, the cassette being removably mounted to the inner portion of the tool body, the tool body having an outer shaft and an inner shaft, the inner shaft being rotatably received in the outer shaft, the inner shaft comprising a flexible joint between the inner and outer portions, the inner shaft driving the drive shaft of the cassette.

18. The implant assembly of claim 17, wherein the actuator is located between the inner and outer portions, the actuator varying the angular orientation of the inner portion with respect to the outer portion.

19. The implant assembly of claim 17, wherein the inner portion includes an attachment end facing the outer portion and the inner portion includes a cassette end opposite the attachment end, the cassette being removably mounted to the cassette end of the inner portion.

20. The implant assembly of claim 17, wherein the flexible joint constitutes a flexible drive element configured to be oriented along a non-linear path.

21. The implant assembly of claim 17, wherein the actuator is located between the inner and outer portions, the actuator comprises a link extending between a base and a head, the base coupled to the outer portion and the head coupled to the inner portion, the head being coupled to the base at a pivot pin, the link being movable with respect to the head and the base to rotate the head about the pivot pin to change an angular orientation of the head with respect to the base.

22. The implant assembly of claim 17, wherein the flexible joint comprises a plurality of hex adapters having hexagon shaped openings that receive a drive end of an hex adapter, the drive end having a plurality of flats that engage the flats of the hexagon shaped opening, the hex adapters being configured to be positioned at a plurality of angles within the corresponding opening of the adjacent the hex adapter.

23. An implant assembly comprising:
an outer shaft extending along a longitudinal axis between a first end and a second end;
an actuator separately manufactured from, and coupled to the second end of the outer shaft, the actuator having a base and a head movable with respect to the base, the base being coupled to the second end, the head being configured to hold a removable cassette used for setting and distracting an implant, the head being movable with respect to the second end to change an angle of orientation of the cassette with respect to the longitudinal axis; and
an inner shaft rotatably received in the outer shaft, the inner shaft comprising a driver coupled to a handle at one end of the driver and coupled to a flexible joint at the other end of the driver, the flexible joint extending through the base and head of the actuator, wherein the flexible joint is configured to transfer the rotation of the driver to the cassette for distracting the implant.

24. The implant assembly of claim 23, wherein the flexible joint constitutes a flexible drive element configured to be oriented along a non-linear path.

25. The implant assembly of claim 23, wherein the head is pivotably coupled to the base at a pivot pin.

26. The implant assembly of claim 23, wherein the actuator comprises a link extending between the base and the head, the head being coupled to the base at a pivot pin, the link being movable with respect to the head and the base to rotate the head about the pivot pin to change an angular orientation of the head with respect to the base.

27. The implant assembly of claim 23, further comprising a slide coupled to the head, the slide being moved along the longitudinal axis to change the position of the head with respect to the base.

28. The implant assembly of claim 27, further comprising a slide handle coupled to the slide, the slide handle located proximate to the first end of the outer shaft, the slide handle being operated to control the position of the slide.

29. The implant assembly of claim 23, wherein the flexible joint comprises a plurality of hex adapters having hexagon shaped openings that receive a drive end of an hex adapter, the drive end having a plurality of flats that engage the flats of the hexagon shaped opening, the hex adapters being configured to be positioned at a plurality of angles within the corresponding opening of the adjacent the hex adapter.

30. The implant assembly of claim 23, further comprising a cassette threadably coupled to and supported by the head, the cassette being removable from the head such that the cassette is configured to be removed and replaced by a different cassette, the cassette having a housing, a gear held by the housing, and a drive shaft driving the gear, the drive shaft being driven by the flexible joint.

31. The implant assembly of claim 30, further comprising an implant held by the cassette, the implant comprising an upper element and a lower element coaxially aligned with one another, the upper and lower elements being configured to be displaced relative to one another along a longitudinal axis of the implant by the gear.

* * * * *